US010364073B2

(12) United States Patent
Paganuzzi

(10) Patent No.: US 10,364,073 B2
(45) Date of Patent: Jul. 30, 2019

(54) DISPENSER

(71) Applicant: BORMIOLI PHARMA S.R.L., Milan (IT)

(72) Inventor: Valerio Paganuzzi, Parma (IT)

(73) Assignee: BORMIOLI PHARMA S.P.A., Milan (IT)

( * ) Notice: Subject to any disclaimer, the term of this patent is extended or adjusted under 35 U.S.C. 154(b) by 104 days.

(21) Appl. No.: 15/311,681

(22) PCT Filed: May 27, 2015

(86) PCT No.: PCT/IB2015/053948
§ 371 (c)(1),
(2) Date: Nov. 16, 2016

(87) PCT Pub. No.: WO2015/181730
PCT Pub. Date: Dec. 3, 2015

(65) Prior Publication Data
US 2017/0096266 A1    Apr. 6, 2017

(30) Foreign Application Priority Data
May 27, 2014   (IT) .............................. PR2014A0033

(51) Int. Cl.
*A61F 9/00* (2006.01)
*B05B 11/04* (2006.01)
*B65D 47/20* (2006.01)

(52) U.S. Cl.
CPC ........ *B65D 47/2075* (2013.01); *A61F 9/0008* (2013.01); *B05B 11/047* (2013.01)

(58) Field of Classification Search
CPC .... B65D 47/2075; B65D 47/18; A61F 11/047
USPC .......................................... 222/212; 137/511
See application file for complete search history.

(56) References Cited

U.S. PATENT DOCUMENTS

| 4,739,906 A * | 4/1988 | LoTurco ............... A61J 1/1443 |
| | | 222/212 |
| 8,408,433 B2 * | 4/2013 | Fontana ............. B65D 47/2068 |
| | | 222/107 |
| 8,499,985 B2 * | 8/2013 | Lehmkuhl .......... B65D 47/2068 |
| | | 222/153.14 |
| 2002/0005415 A1 | 1/2002 | De Laforcade |

(Continued)

FOREIGN PATENT DOCUMENTS

| DE | 43 16 316 A1 | 11/1994 |
| DE | 10 2009 048 476 B3 | 9/2010 |
| EP | 0 500 249 A1 | 8/1992 |

(Continued)

*Primary Examiner* — Jeremy Carroll
(74) *Attorney, Agent, or Firm* — Jeffrey N. Townes; Cozen O'Connor

(57) ABSTRACT

A dispenser for dispensing a liquid or viscous product, comprising a dispensing valve (2). The dispensing valve, in turn, comprises: —product sealing/releasing means (21), which in a first configuration prevents outflow of the product from the dispenser and in a second configuration enables outflow of the product from the dispenser; —elastic return means (22) for returning the sealing means (21) to the first configuration from the second configuration. The elastic return means (22) and at least part of the product sealing/releasing means (21) are integrated in the same body (20).

17 Claims, 3 Drawing Sheets

(56) References Cited

U.S. PATENT DOCUMENTS

2011/0079300 A1* 4/2011 Kneer .................... B65D 47/18
            137/511
2015/0216723 A1  8/2015 Yoshimura et al.

FOREIGN PATENT DOCUMENTS

| EP | 1 145 981 A1 | 10/2001 |
| EP | 1 291 288 A2 | 3/2003 |
| EP | 1 982 929 A2 | 10/2008 |
| WO | 89/01104 A1 | 2/1989 |
| WO | 94/26612 A2 | 11/1994 |
| WO | 2013/168244 A1 | 11/2013 |

* cited by examiner

DISPENSER

CROSS-REFERENCE TO RELATED APPLICATIONS

This application is a national-stage application under 35 U.S.C. § 371 of PCT Application No. PCT/IB2015/053948, filed May 27, 2015, which claims benefit of priority to Italian Patent Application No. PR2014A000033, filed May 27, 2014, both of which are hereby incorporated by reference in their entirety.

TECHNICAL FIELD

The object of the present invention is a dispenser for dispensing a liquid or viscous product.

STATE OF THE ART

There are known dispensers for dispensing ophthalmic solutions and comprising:
a container for the product to be dispensed;
a dispenser spout located at one end of the container.

The product is forced to pass through a specific narrow section of the spout so as to be dispensed. For this purpose, a user applies pressure with his/her fingers. This bends the walls of the container, increasing the pressure therein and enabling outflow of the product. After the product has been released, the walls of the container return to the undeformed configuration and outside air enters the container to equilibrate the pressures.

However, the air entering the container jeopardizes proper preservation of the product contained therein.

In an alternative solution, the dispenser comprises a dispensing valve that is opened by an increase in the internal pressure, whereas the task of bringing the valve back into the closed configuration is entrusted to an added metal spring. In this case, air does not enter the dispenser through said valve, but is drawn through a secondary opening that forces the passage of the air through a dedicated filter. Although it is filtered, the air still remains a possible vector for entry of microorganisms that contaminate the product and the action of which would in any case jeopardize proper preservation of the product.

One drawback of this design is related to its complexity, which thus requires high production costs and a structural complexity that negatively affects the sturdiness of the kinematic mechanisms for opening and closing the valve.

AIM OF THE INVENTION

In this context, the technical task underlying the present invention is to optimize the components of the dispenser. In this regard, the aim of the present invention is to offer a sturdy dispenser that protects the product contained therein from the action of external microorganisms.

The defined technical task and the specified aims are substantially achieved by a dispenser comprising the technical characteristics set forth in one or more of the appended claims.

BRIEF DESCRIPTION OF THE DRAWINGS

Further characteristics and advantages of the present invention will become more apparent from the approximate, and thus non-limiting, description of a preferred, but not exclusive, embodiment of a dispenser as illustrated in the accompanying drawings, of which.

DETAILED DESCRIPTION OF PREFERRED EMBODIMENTS OF THE INVENTION

Figure 1:
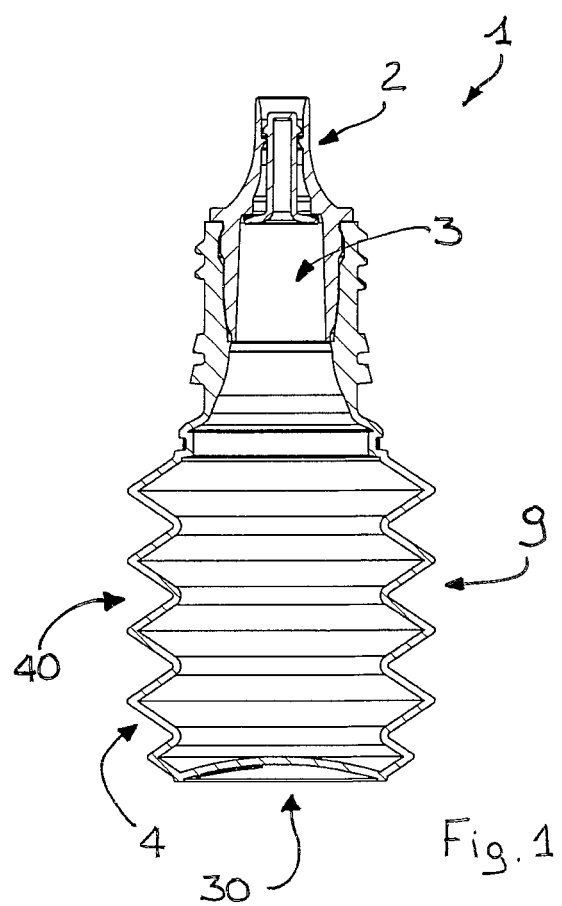
FIG. 1 is a sectional view of a dispenser according to the present invention.
Figure 3:
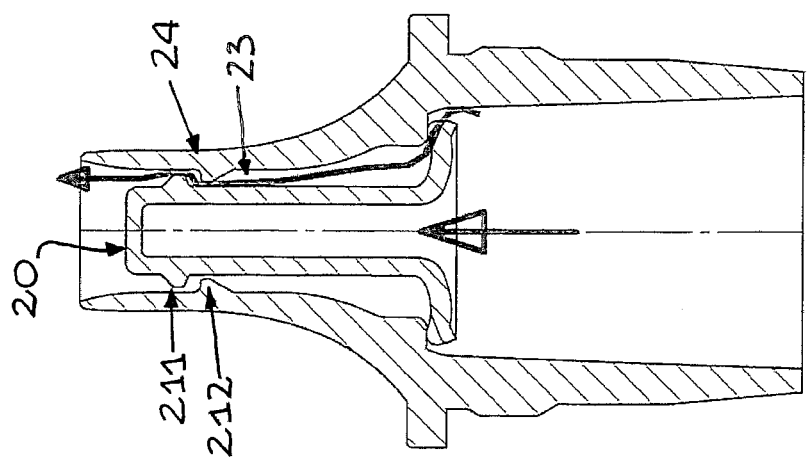
FIG. 3 illustrates a second configuration of the dispenser of FIG. 1.
Figure 2:
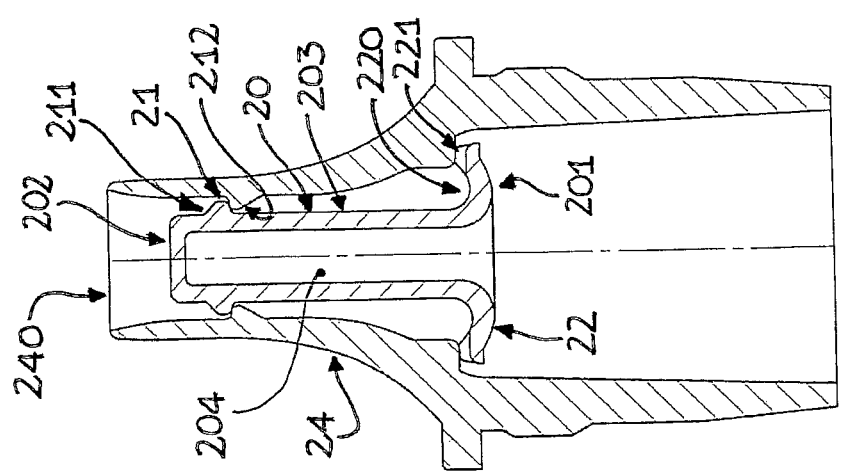
FIG. 2 illustrates a first configuration of the dispenser of FIG. 1.

A dispenser for dispensing a liquid or viscous liquid (typically a pharmaceutical product) is indicated by reference number 1 in the accompanying figures. In more general terms, the liquid or viscous liquid could consist of a non-gaseous fluid. Preferably, but not necessarily, this dispenser 1 consists of a dropper. For example, this dispenser 1 could be utilized to dispense ophthalmic solutions or other solutions. However, it could also be used to dispense a cream or similar products.

The dispenser 1 comprises a dispensing valve 2.

The dispenser 1 advantageously comprises a product reservoir 3 that is in fluid communication with said valve 2.

This valve 2 in turn comprises product sealing/releasing means 21.

In a first configuration, the sealing/releasing means 21 prevents outflow of the product from the dispenser (thus performing an action of fluid dynamic sealing of the product). At the same time, in the first configuration, the sealing/releasing means 21 defines a barrier that at least temporarily blocks entry of external air. In particular, in the first configuration of the sealing means 21, the reservoir 3 is sealed with respect to the entry of microorganisms present in the external air. This therefore makes it possible to minimize the risk of the product coming into contact with microorganisms that can damage the chemical characteristics and the active ingredients thereof. In the first configuration, the sealing means 21 performs a slowing-down action (if not completely sealed), with respect to the entry of external air in the reservoir 3. This is very important given that it makes it possible to avoid adding preservatives to the product (therefore contraindications linked to the use of such preservatives are avoided and it is possible to save on costs).

In a second configuration, the sealing/releasing means 21 enables outflow of the product from the dispenser. The fluid dynamic sealing action realized by the sealing/releasing means 21 takes places along an annular surface (limited in thickness, for example less than 1 or 2 millimeters). The fluid dynamic sealing action is therefore quite localized.

The dispensing valve 2 further comprises elastic return means 22 for returning the sealing means 21 to the first configuration from the second configuration.

The elastic return means 22 and at least part of the product sealing/releasing means 21 are integrated in the same body 20. The elastic return means 22 and at least part of the sealing means 21 are distinct parts that are part of the same component realized as a single piece in a single body. In the preferred solution, said body 20 is made of a deformable material, for example an elastomeric material. The elastic return means 22 is afforded solely in said body 20.

The valve 2 comprises a casing 24 that encases at least one part of said body 20. This casing 24 is rigid. In particular, it could be made of plastic. The casing 24 conveniently encases the entire body 20. In particular, the casing 24 encases the entire body when the sealing/releasing means 21 is in the first configuration. Likewise, the casing 24 encases the entire body 20 also when the sealing/releasing means 21 is in the second configuration. In any position assumed by the body 20 in the second configuration, said entire body 20 thus remains inside the casing 24.

The sealing/releasing means 21 comprises:
a projection 211 that is part of said body 20;
abutment means 212 for abutting against said projection 211.

The abutment means 212 is integral with said casing 24 so as to realize, together with the projection 211, fluid dynamic sealing of the product (and also sealing that prevents microorganisms present in the external air from traveling through the valve 2). The abutment means 212 is preferably made as a single piece with said casing.

In the first configuration of the sealing/releasing means 21, the projection 211 is in contact with the abutment means 212.

A dispenser channel 23 for dispensing the product extends between said body 20 and said casing 24 (to be more specific, it extends in the space between the body 20 and the casing 24). In the first configuration, the projection 211 and the abutment means 212 obstruct said dispenser channel 23.

This dispenser channel 23 has an annular passage section. This facilitates homogeneous dispensation of the product.

The projection 211 and the abutment means 212 also extend annularly. In particular, the projection 211 and the abutment means 212 jointly realize fluid dynamic sealing along an annular surface.

As mentioned previously, the dispenser 1 advantageously comprises a product reservoir 3 that is in fluid communication with said valve 2. At least in the second configuration of the sealing/releasing means 21, the abutment means 212 is interposed between said to projection 211 and said reservoir 3. This conveniently occurs in the first configuration of the sealing/releasing means 21 as well.

The elastic return means 22 comprises a concavity 220. This concavity 220 extends along an annular line. The concavity 220 advantageously faces the sealing/releasing means 21. The elastic return means 22 defines a type of Belleville spring (substantially defined by the concavity 220).

Figure 4:
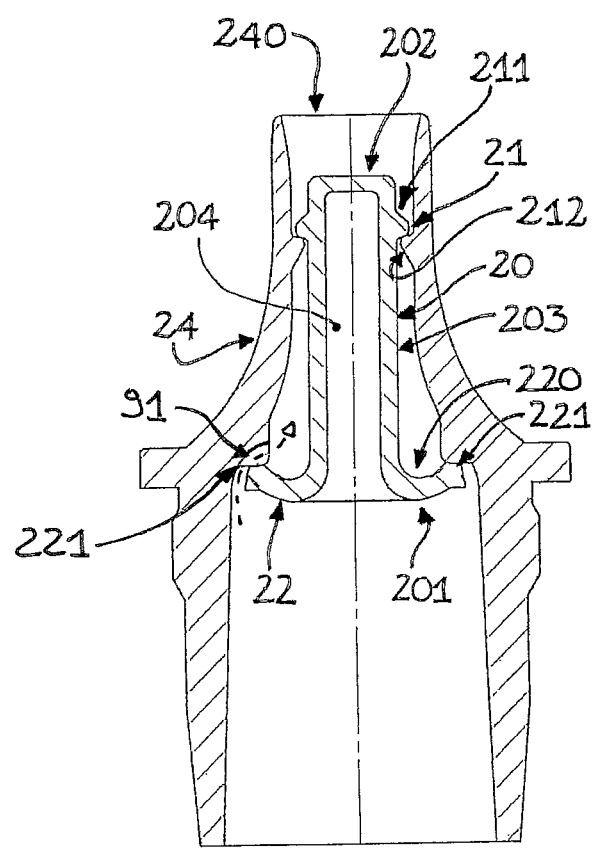
FIG. 4 is an alternative solution to that appearing in FIG. 2.

The concavity 220 is found at one end of said dispenser channel 23. More specifically, the concavity 220 extends in proximity to an inlet of the dispenser channel 23. It represents an interface between the reservoir 3 and the dispenser channel 23. Preferably at said concavity 220, the dispenser 1 (particularly the body 20) comprises at least one opening 221 for passage of the product from said reservoir 3 to said dispenser channel 23. Conveniently, this opening 221 is open at all times. The opening cannot be blocked by a component of the dispenser 1. This opening is advantageously afforded in the casing 24. In particular, this opening comprises a groove 91 that is afforded in the casing and that makes it possible to set the dispenser channel 23 in communication with the reservoir 3 (see FIG. 4). Advantageously, the dispenser 1, particularly the body 20, comprises a plurality of openings 221 for passage, which are advantageously distributed along the annular line of extension of the cavity. The dispenser channel 23 conveniently has an annular section at least along the entire tract extending from said concavity 222 to the sealing/releasing means 21.

The concavity 220 conveniently decreases when the sealing/releasing means 21 passes from the first the second configuration.

The body 20 comprises:
a base 201 that defines anchorage to remaining parts of the dispenser 1; (the elastic return means 22 is advantageously located at said base 201 and the anchorage typically comprises an enlargement resting on a mouth of the casing 24);
one end 202 that is opposite said base 201 (advantageously, in the second configuration of the sealing/releasing means 21, this end 202 is closer to a dispenser hole 240 afforded in said casing 24, compared to its position in the first configuration);
a shank 203 that extends between the base 201 and said opposite end 202 (this shank is preferably cylindrical).

The body 20 is typically shaped like a mushroom. The return means 22 is integrated in the cap of the mushroom (this cap coincides with the anchorage described previously). Said projection 221 is integrated along a stem of the mushroom (this stem substantially coincides with said shank 203).

The shank 203 could have a cavity 204 in fluid communication with the reservoir 3. In an unillustrated alternative solution, the shank 203 could have a divider that prevents fluid communication between the interior of the shank 203 and the reservoir 3.

The dispenser 1 further comprises pressure increasing means 4 for increasing the pressure in said reservoir 3. The pressure increasing means 4 is accessible to the user from the exterior of the reservoir 3. An increase in pressure in the reservoir 3 determines passage of the sealing/releasing means 21 from the first to the second configuration. In particular, an increase in pressure brings about a distancing of said projection 211 from the abutment means 212 with resulting dispensation of the product. In particular, the increase in pressure brings about an elongation of the body 20.

The pressure increasing means 4 is preferably activated manually, typically by a user's finger. The pressure increasing means 4 advantageously comprises a collapsible wall. For example, the pressure increasing means 4 (or in any case, the collapsible wall) comprises a bellows 40 that is manually activated and located along a wall of the reservoir 3. In fact, compression of the collapsible wall brings about an increase in pressure in the reservoir 3. Advantageously, the pressure increasing means 4 and the valve 2 are found at two opposite ends of the dispenser 1.

In the preferred solution, the dispenser 1 comprises only three separate pieces: said casing 24, said body 20 and a bottom 30 that incorporates the pressure increasing means 4 (said bottom 30, said casing 24 and said body 20 delimit said reservoir 3).

The dispenser 1 conveniently comprises a container 9 for the product to be dispensed; this container 9 conveniently comprises said bottom 30. The casing 24 is partially inserted in the container 9. More specifically, it is applied to one end of the container 9. At least one annular gasket is interposed between the casing 24 and the part of the container 9 in which the casing 24 is inserted. The body 20 is not in contact with the container. This container is conveniently made of a plastic material.

The operation of the invention is conveniently illustrated herein below.

The sealing/releasing means 21 is initially found in the first configuration. The projection 211 and the abutment means 212 are thus in contact with each other. In this manner, fluid dynamic sealing is realized, preventing the dispenser 1 from dispensing the product. In this configuration, entry of microorganisms into the reservoir 3 is prevented, thereby protecting the product contained therein. Moreover, in this configuration, the dispenser 1 defines a barrier that at least temporarily delays entry of air in the reservoir 3. The dispenser 1 conveniently lacks a ventilation hole, which in the first configuration of the sealing/releasing means 21 allows air to enter the reservoir 3. The user can increase the pressure in the reservoir 3 by manually intervening on the pressure increasing means 4 (the collapsible wall). This increase in pressure determines passage of the sealing/releasing means 21 from the first to the second configuration. In particular, the projection 211 is distanced from the abutment means 212, thereby permitting dispensation of the product. When the user releases the collapsible wall, the sealing/releasing means 21 instantly returns to the first configuration owing to the action of the elastic return means 22. In this manner, dispensation of the product is interrupted and entry of external air into the reservoir 3 is also prevented.

The invention thus conceived makes it possible to achieve multiple advantages.

Firstly, it allows for optimal preservation of the product present inside the dispenser 1 without requiring the use of specific preservatives.

At the same time, this result is achieved with a dispenser whose components have been optimized for the purpose of realizing a structure offering reduced costs and that is very sturdy (as it has no delicate kinematic mechanisms for dispensing the product).

The invention thus conceived is susceptible to numerous modifications and variants, all of which falling within the scope of the inventive concept characterizing the invention. Moreover, all details may be replaced with other technically equivalent elements. All the materials used, as well as the dimensions, may in practice be of any type, according to needs.

The invention claimed is:

1. A dispenser (1) for dispensing a liquid or viscous product, comprising a dispensing valve (2), in turn, comprising:
   product sealing/releasing means (21), which in a first configuration prevents outflow of the product from the dispenser and in a second configuration enables outflow of the product from the dispenser;
   elastic return means (22) for returning the sealing means (21) to the first configuration from the second configuration; the elastic return means (22) and at least part of the product sealing/releasing means (21) being integrated in a body (20);
   a casing (24) that encases at least one part of said body (20);
   a dispenser channel (23) for dispensing the product that extends between said body (20) and said casing (24); the elastic return means (22) comprising an annular concavity (220) positioned at one end of said dispenser channel (23);
   the dispenser (1) comprising:
   a reservoir (3) that is in fluid communication with said valve (2);
   at least one opening (221) for passage of the product from said reservoir (3) to said dispenser channel (23); said opening (221) being open at all times so that it cannot be blocked by a component of the dispenser (1);
   the body (20) comprising:
   a base (201) that defines anchorage to remaining parts of the dispenser (1);
   one end (202) that is opposite said base (201);
   a shank (203) that extends between the base (201) and said opposite end (202); the shank (203) having a cavity (204) in fluid communication with the reservoir (3);
   wherein the opening (221) comprises a groove (91) afforded in the casing (24).

2. The dispenser according to claim 1, wherein said dispenser channel (23) has an annular passage section.

3. The dispenser according to claim 1, wherein the sealing/releasing means (21) comprises:
   a projection (211) that is part of said body (20);
   abutment means (212) for abutting against said projection (211), said abutment means (212) being afforded in said casing (24) and defines fluid dynamic sealing means of the product; in the first configuration of the sealing/releasing means (21), said projection (211) is in contact with the abutment means (212).

4. The dispenser according to claim 3, wherein said projection (211) and said abutment means (212) extend annularly.

5. The dispenser according to claim 1, wherein, in any position assumed by the body (20) in the second configuration, said body (20) remains inside the casing (24).

6. The dispenser according to claim 1, wherein, in the first configuration of the sealing means (21), said reservoir (3) is sealed with respect to entry of microorganisms present in the external air.

7. The dispenser according to claim 6, wherein the dispenser comprises pressure increasing means (4) for increasing the pressure in said reservoir (3), said pressure increasing means (4) being accessible to the user from the exterior of the reservoir (3); an increase in the pressure in the reservoir (3) determining passage of the sealing/releasing means (21) from the first to the second configuration; the pressure increasing means (4) comprising a collapsible wall that can be manually activated and that delimits the reservoir (3) at least partially.

8. The dispenser according to claim 6, wherein, in the first configuration, the product sealing/releasing means (21) defines a barrier that slows down entry of external air in the reservoir (3).

9. The dispenser according to claim 1, wherein said concavity (220) faces the sealing/releasing means (21).

10. The dispenser according to claim 9, wherein, in the first configuration of the sealing means (21), said reservoir (3) is sealed with respect to entry of microorganisms present in the external air.

11. The dispenser according to claim 1, wherein the dispenser comprises a container (9) for the product to be dispensed.

12. The dispenser according to claim 11, wherein the casing (24) is partially inserted in the container (9); and the body (20) is not in contact with the container (9).

13. The dispenser according to claim 11, wherein the container (9) is made of a plastic material.

14. The dispenser according to claim 1, wherein the concavity (220) of the elastic return means (22) defines a Belleville spring.

15. The dispenser according to claim 1, wherein the elastic return means (22) and at least part of the sealing means (21) are different parts of the body (20), said body being a single piece.

16. A dispenser (1) for dispensing a liquid or viscous product, comprising a dispensing valve (2), in turn, comprising:
   product sealing/releasing means (21), which in a first configuration prevents outflow of the product from the dispenser and in a second configuration enables outflow of the product from the dispenser;

elastic return means (22) for returning the sealing means (21) to the first configuration from the second configuration; the elastic return means (22) and at least part of the product sealing/releasing means (21) being integrated in a same body (20);

a casing (24) that encases at least one part of said body (20);

a dispenser channel (23) for dispensing the product that extends between said body (20) and said casing (24); the elastic return means (22) comprising an annular concavity (220) positioned at one end of said dispenser channel (23);

the dispenser (1) comprising:

a reservoir (3) that is in fluid communication with said valve (2);

at least one opening (221) for passage of the product from said reservoir (3) to said dispenser channel (23); said opening (221) being open at all times so that it cannot be blocked by a component of the dispenser (1);

a container (9) for the product to be dispensed;

the body (20) comprising:

a base (201) that defines anchorage to remaining parts of the dispenser (1);

one end (202) that is opposite said base (201);

a shank (203) that extends between the base (201) and said opposite end (202); the shank (203) having a cavity (204) in fluid communication with the reservoir (3);

wherein the casing (24) is partially inserted in the container (9); and the body (20) is not in contact with the container (9).

17. The dispenser according to claim 16, wherein the container (9) is made of a plastic material.

* * * * *